United States Patent
Kramer

(10) Patent No.: US 12,053,397 B2
(45) Date of Patent: *Aug. 6, 2024

(54) TRACHEOBRONCHIAL Y-STENTS, DELIVERY CATHETERS AND DELIVERY APPARATUS, AND METHODS FOR DELIVERING BRONCHIAL Y-STENTS

(71) Applicant: George Kramer, Westbury, NY (US)

(72) Inventor: George Kramer, Westbury, NY (US)

(*) Notice: Subject to any disclaimer, the term of this patent is extended or adjusted under 35 U.S.C. 154(b) by 250 days.

This patent is subject to a terminal disclaimer.

(21) Appl. No.: 17/316,570

(22) Filed: May 10, 2021

(65) Prior Publication Data

US 2021/0259862 A1 Aug. 26, 2021

Related U.S. Application Data

(63) Continuation of application No. 16/212,629, filed on Dec. 6, 2018, now abandoned, which is a continuation of application No. 15/169,509, filed on May 31, 2016, now Pat. No. 10,179,057.

(60) Provisional application No. 62/167,882, filed on May 28, 2015.

(51) Int. Cl.
| | | |
|---|---|---|
| *A61F 2/97* | (2013.01) | |
| *A61F 2/82* | (2013.01) | |
| *A61F 2/90* | (2013.01) | |
| *A61F 2/954* | (2013.01) | |
| *A61F 2/04* | (2013.01) | |
| *A61F 2/06* | (2013.01) | |
| *A61F 2/95* | (2013.01) | |

(52) U.S. Cl.
CPC .............. *A61F 2/90* (2013.01); *A61F 2/954* (2013.01); *A61F 2002/043* (2013.01); *A61F 2002/065* (2013.01); *A61F 2/9522* (2020.05); *A61F 2210/0014* (2013.01); *A61F 2230/006* (2013.01)

(58) Field of Classification Search
CPC ...... A61F 2/954; A61F 2002/065; A61F 2/95; A61F 2/82; A61F 2/97; A61F 2/011; A61F 2/90; A61F 2/9522
See application file for complete search history.

(56) References Cited

U.S. PATENT DOCUMENTS

| | | | |
|---|---|---|---|
| 3,818,515 A | 6/1974 | Neville | |
| 4,662,404 A | 5/1987 | LeVeen | |
| 5,609,627 A | 3/1997 | Goicoechea et al. | |
| 5,662,674 A | 9/1997 | Debbas | |
| 5,676,697 A | 10/1997 | McDonald | |
| 5,906,640 A | 5/1999 | Penn et al. | |
| 6,019,787 A * | 2/2000 | Richard | A61F 2/95 606/194 |
| 6,117,117 A | 9/2000 | Mauch | |
| 6,254,628 B1 * | 7/2001 | Wallace | A61B 17/1214 606/108 |
| 6,261,273 B1 | 7/2001 | Ruiz | |

(Continued)

FOREIGN PATENT DOCUMENTS

WO WO-0013613 A1 * 3/2000 ............. A61F 2/954

*Primary Examiner* — Seema Mathew
(74) *Attorney, Agent, or Firm* — Daniel P. Burke & Associates, PLLC; Daniel P. Burke

(57) ABSTRACT

Y-stents and delivery apparatus for delivering the Y-stents include a delivery catheter with an open distal end having two, circumferentially opposed extensions separated by two receiving portions which receive an anatomical junction.

7 Claims, 24 Drawing Sheets

(56) References Cited

U.S. PATENT DOCUMENTS

| | | | | |
|---|---|---|---|---|
| 6,352,561 | B1* | 3/2002 | Leopold | A61F 2/07 623/1.11 |
| 6,383,171 | B1* | 5/2002 | Gifford | A61F 2/958 623/1.36 |
| 6,409,750 | B1 | 6/2002 | Hyodoh et al. | |
| 6,514,281 | B1* | 2/2003 | Blaeser | A61F 2/954 623/1.35 |
| 6,827,731 | B2* | 12/2004 | Armstrong | A61F 2/95 623/1.12 |
| 7,074,235 | B1 | 7/2006 | Roy | |
| 7,169,177 | B2* | 1/2007 | Obara | A61F 2/91 623/1.35 |
| 7,545,321 | B2 | 6/2009 | Silvestri et al. | |
| 7,641,684 | B2* | 1/2010 | Hilaire | A61F 2/954 623/1.35 |
| 8,545,544 | B2* | 10/2013 | Spenser | A61B 17/12022 623/1.11 |
| 8,641,752 | B1* | 2/2014 | Holm | A61F 2/966 623/1.12 |
| 9,474,640 | B2* | 10/2016 | Johnson | A61F 2/954 |
| 11,540,933 | B2* | 1/2023 | Honeyfield | A61F 2/9661 |
| 11,911,305 | B2* | 2/2024 | Smith | A61F 2/966 |
| 2001/0004706 | A1 | 6/2001 | Hojeibane | |
| 2001/0016767 | A1* | 8/2001 | Wilson | A61F 2/954 623/1.11 |
| 2002/0111674 | A1 | 8/2002 | Chouinard et al. | |
| 2003/0024534 | A1 | 2/2003 | Silvestri et al. | |
| 2004/0249433 | A1* | 12/2004 | Freitag | A61F 2/95 606/108 |
| 2005/0043779 | A1 | 2/2005 | Wilson | |
| 2005/0234542 | A1 | 10/2005 | Melsheimer | |
| 2006/0293695 | A1* | 12/2006 | Ricci | A61F 2/958 623/1.11 |
| 2008/0167705 | A1* | 7/2008 | Agnew | A61F 2/95 623/1.12 |
| 2008/0208309 | A1 | 8/2008 | Saeed | |
| 2009/0248130 | A1 | 10/2009 | Boylan | |
| 2010/0131038 | A1 | 5/2010 | Milijasevic et al. | |
| 2010/0249907 | A1* | 9/2010 | Dorn | A61F 2/97 623/1.23 |
| 2011/0046720 | A1 | 2/2011 | Shalev et al. | |
| 2011/0054586 | A1 | 3/2011 | Mayberry | |
| 2011/0077730 | A1* | 3/2011 | Fenster | A61F 2/97 623/1.23 |
| 2012/0109279 | A1 | 5/2012 | Mayberry et al. | |
| 2013/0103163 | A1 | 4/2013 | Krimsky et al. | |
| 2013/0226279 | A1* | 8/2013 | Slattery | A61F 2/958 623/1.12 |
| 2014/0148891 | A1* | 5/2014 | Johnson | A61F 2/954 623/1.11 |

\* cited by examiner

TRACHEOBRONCHIAL Y-STENTS, DELIVERY CATHETERS AND DELIVERY APPARATUS, AND METHODS FOR DELIVERING BRONCHIAL Y-STENTS

RELATED APPLICATION DATA

This application is a continuation of U.S. patent application Ser. No. 16/212,629 filed on Dec. 6, 2018, which is a continuation of U.S. patent Ser. No. 15/169,509 filed on May 31, 2016, now U.S. Pat. No. 10,179,057, which claims the benefit of Provisional Patent Application Ser. No. 62/167,882 filed on May 28, 2015, which are hereby incorporated by reference.

Disclosed are Y-stents, delivery catheters and delivery apparatus for Y-stents, and methods for delivering Y-stents. Disclosed delivery systems are particularly suited for use in the placement of stents at junctions within bronchi, such as at the junction of the right principal bronchus (RPB) and left principal bronchus (LPB), and at the junction of the left caudal lobe bronchus (LB2) and the left cranial lobe bronchus (LB1).

BACKGROUND

Various ailments and trauma can lead to the collapse of bronchial airways in humans and other mammals. For example, neoplastic occlusion, or chronic mitral valve disease in dogs often leads to the collapse of the left main bronchial stem.

SUMMARY

Catheters and other devices for delivering Y-stents, such as Y-shaped bronchial stents are disclosed. The bronchial Y-stents are preferably formed of braided or woven nitinol, but other collapsible, biocompatible materials including alloys and polymers are also suitable stent materials. As used in the medical field, the term "Y-stent" indicates a stent having a trunk and two branches. The delivered Y-stent is preferably collapsible into a smaller configuration so that it can be compressed into a delivery catheter and placed within a patient via a transcatheter procedure, and has sufficient inherent shape memory so that when pushed from the delivery catheter the Y-stent takes its original desired shape. The Y-stent is positionable at the junction of two airways and extends from one airway into two branching airways to restore/maintain patency in the airways around that junction. The preferred woven nitinol material provides desired flexibility and allows tissue ingrowth and normal mucociliary clearance. Unlike some, less compressible materials, the nitinol is less likely to cause erosion of the airway and long term problems with mucociliary clearance.

The disclosed delivery apparatus for delivering the Y-stents comprises a delivery catheter with an open distal end having two, circumferentially opposed extensions separated by two receiving portions configured to be positioned over the desired bronchial junction which defines the branch in the airway during placement of the Y-stent. During a placement procedure, the extensions of the delivery catheter are positioned to extend distally of the bronchial junction when the receiving portions at the distal end portion of the delivery catheter receive the bronchial junction.

The "open" or "unobstructed" distal end of the delivery catheter is completely unobstructed by any structure of the delivery system or delivery kit so that the only forces which need to be overcome when deploying the stent from the delivery catheter are the frictional forces between the collapsed Y-stent and the inner walls of the delivery catheter. In other words, the distal end of the delivery catheter is completely unobstructed to minimize or eliminate proximally directed forces on the stent during the withdrawal of the delivery catheter and after the stent has been properly positioned.

Preferred delivery catheters comprise at least one flexible elbow to facilitate placement around bends in the tracheobronchial airways. A preferred delivery system comprises a delivery catheter, a Y-stent, a hollow plunger shaft, and two guide wires. The guide wires both extend through the delivery catheter, the hollow plunger shaft and the trunk of the Y-stent. One guide wire extends through a first branch of the Y-stent while the other guide wire extends through the other branch of the Y-stent. During placement of the Y-stent into a patient, the surgeon extends the guide wires into the two target airways, i.e. with each guide wire going into one airway, to help guide the distal extensions of the delivery catheter and each of the branched legs of the Y-stent into their respective desired positions. The flexible elbow(s) of the delivery catheter facilitate placement of the catheter around any proximal curves and bends, and into the desired airway proximate the junction of the target airways. As used herein, the term "target airways" refers to the branches of the tracheobronchial passages which receive the branches of the Y-stent.

Methods comprise the step of disposing a Y-stent in a delivery catheter, positioning the delivery catheter in an airway proximate a junction and displacing the Y-stent from the delivery catheter at least partially into two airways. One method comprises positioning the receiving portions of the distal end of the delivery catheter over the junction of the airway, e.g. over a portion of the carina, advancing a plunger shaft within the delivery catheter while maintaining the stent in position, then withdrawing the delivery catheter in a manner which permits the branches of the stent to at least partially expand before the trunk of the stent is out of the delivery catheter. The expansion of the branches of the stent before the stent is entirely out of the delivery catheter reduces the tendency for the stent to spring proximally and dislodge from its optimum placement on the bronchial junction. Thus there are three aspects of the disclosed embodiments which facilitate proper placement and minimize the risk of unintended, proximally-directed dislodgement of the Y-stent after it has been positioned over an anatomical junction: the unobstructed distal opening of the delivery catheter, the outwardly directed expansion forces of the stent itself acting on the airways and the plunger shaft.

Another step comprises positioning, preferably pre-positioning, two guide wires through the same lumen of the delivery catheter, through the lumen of the plunger shaft, through the trunk of the Y-stent and one each through the branches of the Y-stent. During surgery, the guide wires are extended distally into the target airways prior to the displacement of the Y-stent from the delivery catheter in order to guide the branches of the Y-stent into the proper airways.

Another method comprises positioning a collapsed stent and two guide wires into a delivery catheter having distal receiving portions, positioning the delivery catheter into a patient, advancing the guide wires, positioning the receiving portions of the distal end of the delivery catheter over the junction of an airway, e.g. over a portion of the carina, advancing a plunger sheath within the delivery catheter to urge the stent at least partially out the distal end of the catheter such that each branch of the stent enters a separate anatomical branch at the target anatomical junction and such that each branch of the stent expands to some extent, then withdrawing the delivery catheter in the proximal direction. During the withdrawing step, the branches of the stent are left in the respective target airways.

DETAILED DESCRIPTION

One preferred use of the methods, apparatus and devices disclosed is to reestablish patency in a patient's airways.

One aspect of the present invention comprises a delivery device for a self-expanding stent, formed in the shape of a Y of woven nitinol wire. The Y-stent is particularly suited for placement within a collapsed or partially collapsed airway via a transcatheter procedure. One stent is particularly suited for placement at a bronchial junction, such as the carina tracheae. The stent is collapsible into a compact configuration and loaded into a delivery catheter along with two guide wires. The separate branches of the Y-stent are positioned distally of the airway junction, with the trunk of the Y-stent positioned proximally of the airway junction. One guide wire is prepositioned through the trunk and one of the branches of the Y-stent while the other guide wire is prepositioned through the trunk and into the other branch of the Y-stent. The proximal ends of the guide wires extend through and out the proximal ends of the delivery catheter and plunger shaft. During the transcatheter procedure and preferably after the distal end of the delivery catheter is near the desired position, each guide wire is moved distally beyond the distal end of each branch of the Y-stent, beyond the distal end of the delivery catheter and into the respective target airways. The surgeon can confirm the proper positioning of the guide wires and the delivery system during the procedure via a bronchoscope.

The Y-stent is preferably positioned within two airways via a transcatheter procedure using a delivery catheter having a distal end comprising two circumferentially opposed extensions separated by two receiving portions designed to be positioned over the desired bronchial junction. The delivery catheter also, optionally, has at least one flexible elbow. After proper positioning of the delivery catheter over the anatomical junction, the stent is deployed into the target bronchial passages of a patient with the aid of a bronchoscope, plunger shaft and two flexible guide wires. With the guide wires positioned in the respective airways, the branches of the Y-stent are urged from the delivery catheter into the two target airways by advancing the plunger shaft within the delivery catheter. The collapsed stent will expand as space provides, i.e. within the distal end of the delivery catheter if larger than the tubular portion of the delivery catheter and after exiting the distal end of the delivery catheter. After the plunger shaft has seated the Y-stent on the bronchial junction, the delivery catheter is withdrawn while the plunger shaft is held in place. During this placement, the stent expands into its original configuration as the delivery catheter is withdrawn to a predetermined position over the plunger shaft.

Figure 1:
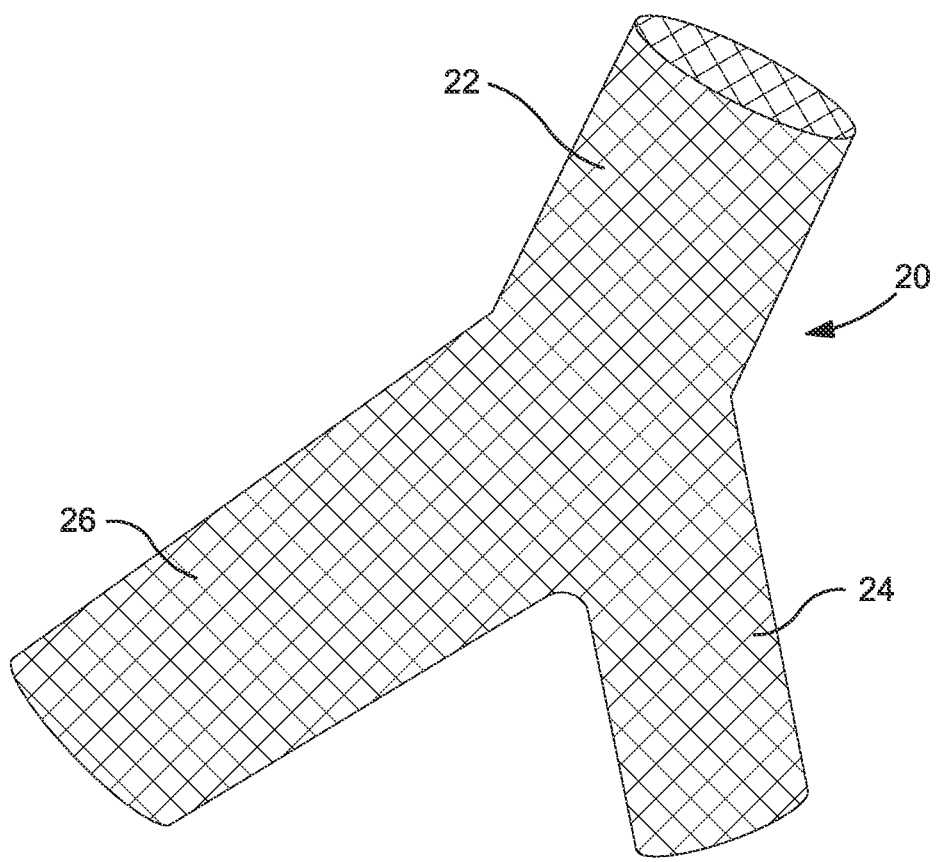
FIG. 1 is a top perspective view of a Y-stent.

FIG. 1 illustrates a collapsible Y-stent 20 comprising a trunk 22, right branch 24 and left branch 26. This Y-stent is preferably hollow and is designed to restore and/or maintain the patency of one or more airways which have wholly or partially collapsed or which are in danger of collapse. In this embodiment, left branch 26 has a greater diameter and is longer than right branch 24 in order to provide a better fit between the Y-stent and the target bronchial branches. This Y-stent is collapsible for ease of delivery to the desired bronchial junction. Y-stent is preferably formed of nitinol wire which has good biocompatibility and shape memory after being collapsed, but can be formed of other materials such as other alloys or polymers.

Figure 2:
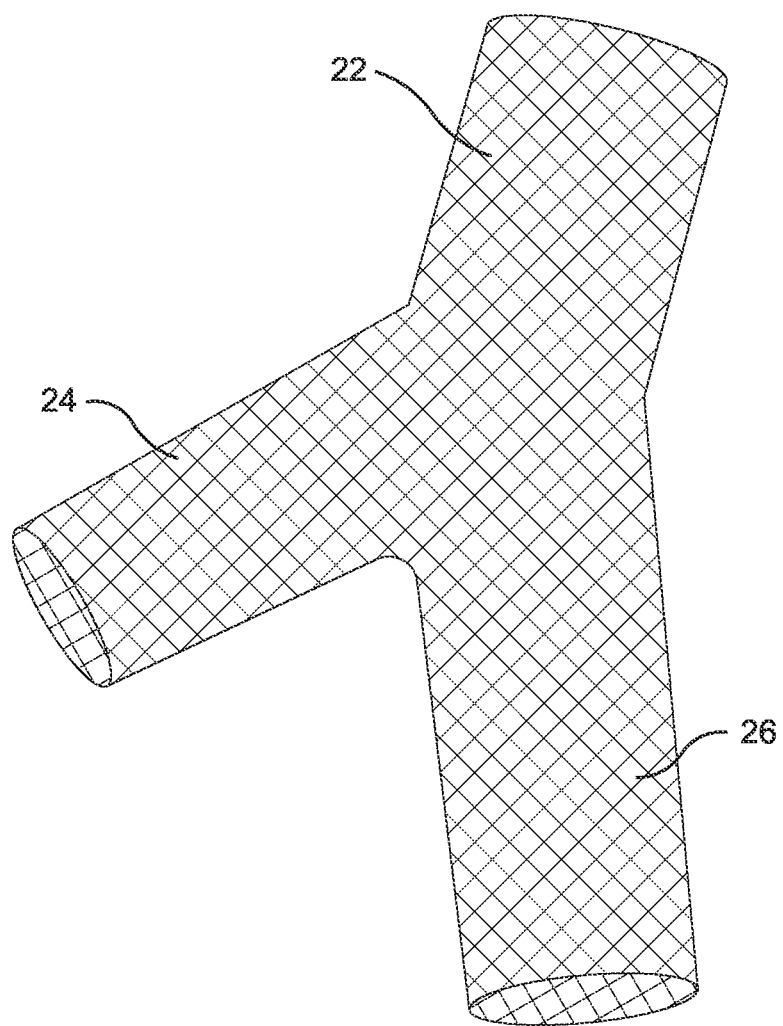
FIG. 2 is a bottom perspective view of the Y-stent of FIG. 1.

FIG. 2 is a rear, distal perspective view of the stent of FIG. 1.

Figure 3:
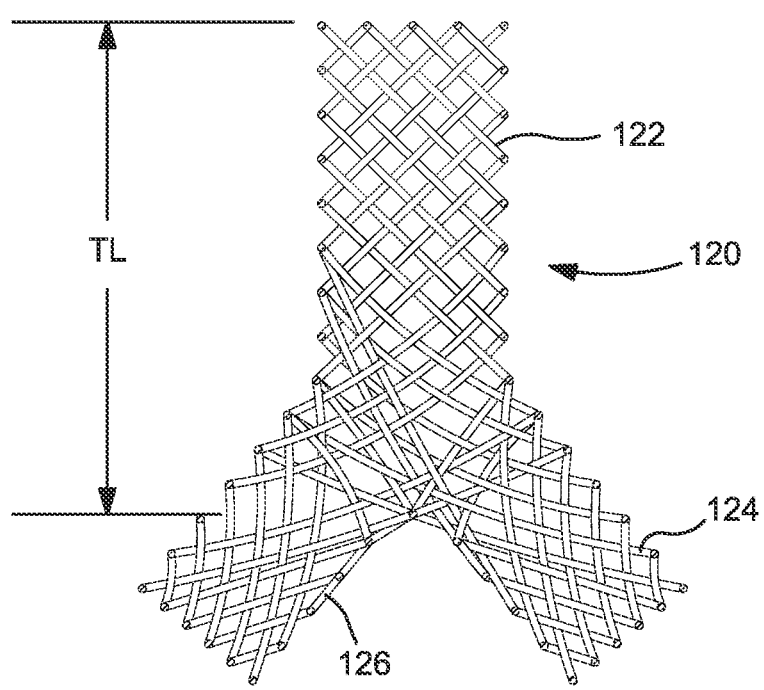
FIG. 3 is a front view of a second Y-stent.

FIG. 3 shows an alternative braided, wire Y-stent 120 comprising a trunk 122, right branch 124 and left branch 126. FIG. 3 also indicates a distance TL which is the distance from the proximal end of a stent to the junction between the stent branches. The significance of TL is explained below.

According to this embodiment, the right branch 124 and left branch 126 are the same length and diameter.

Figure 4:
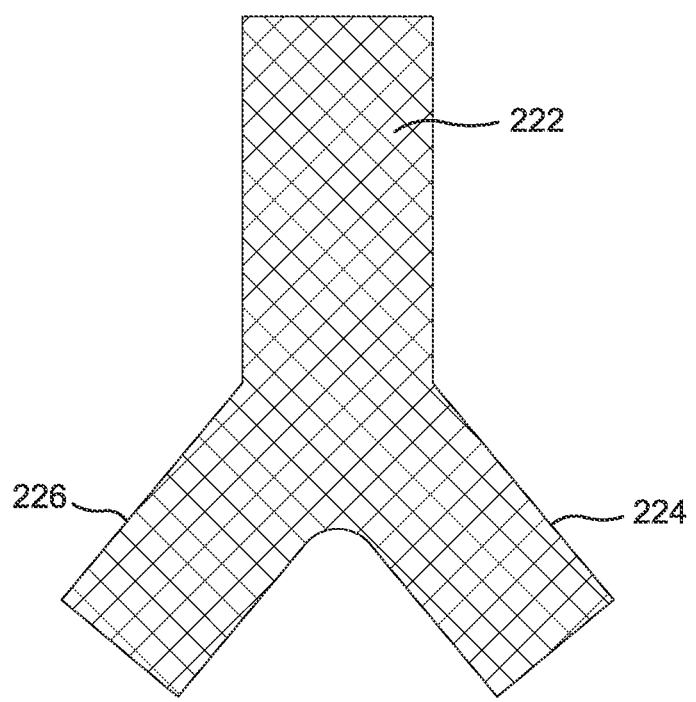
FIG. 4 is front view of a third Y-stent.

FIG. 4 illustrates a third Y-stent comprising a trunk 222 and branches 224 and 226, wherein the branches 224 and 226 are the same configuration (size and shape) as each other, but slightly longer than those of the embodiment of FIG. 3. Thus, the branches of a given Y-stent can be the same or different lengths and/or diameters, and are preferably sized and configured to closely conform to the intended target airways and bronchial junction.

Figure 5:
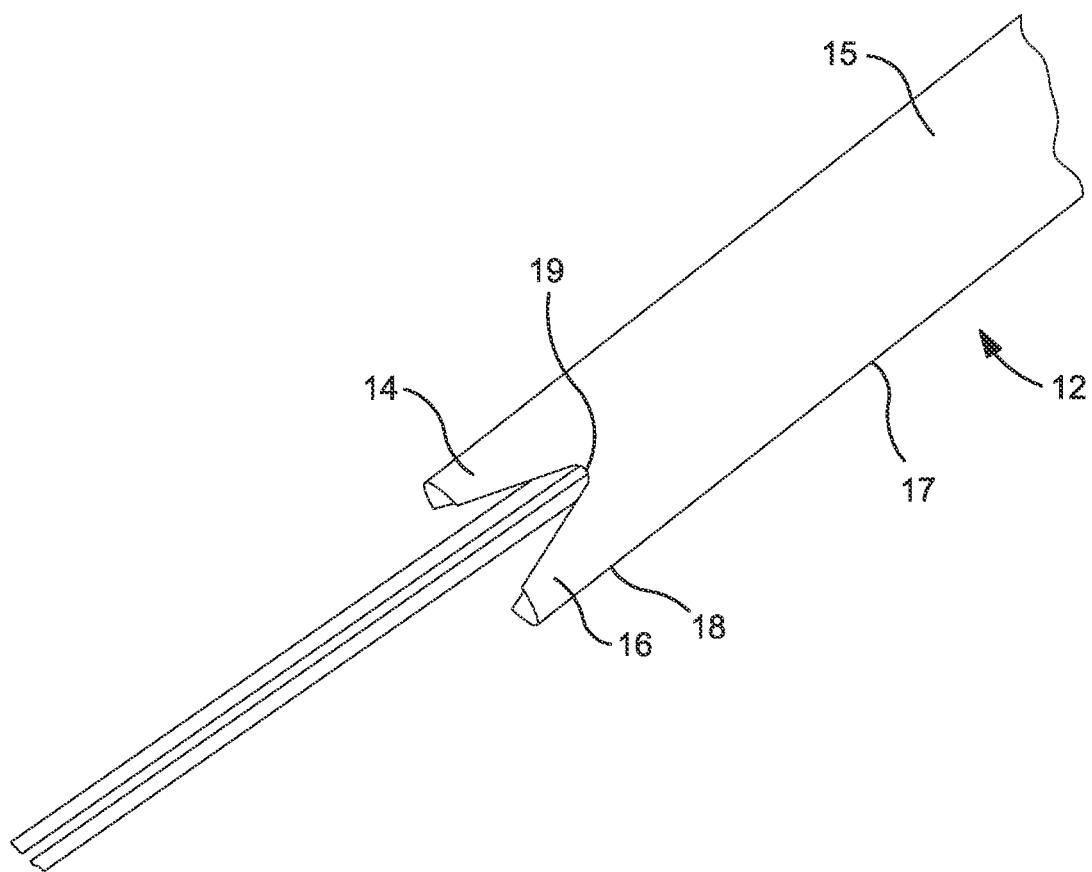
FIG. 5 is a distal, perspective view of a delivery catheter.
Figure 6:
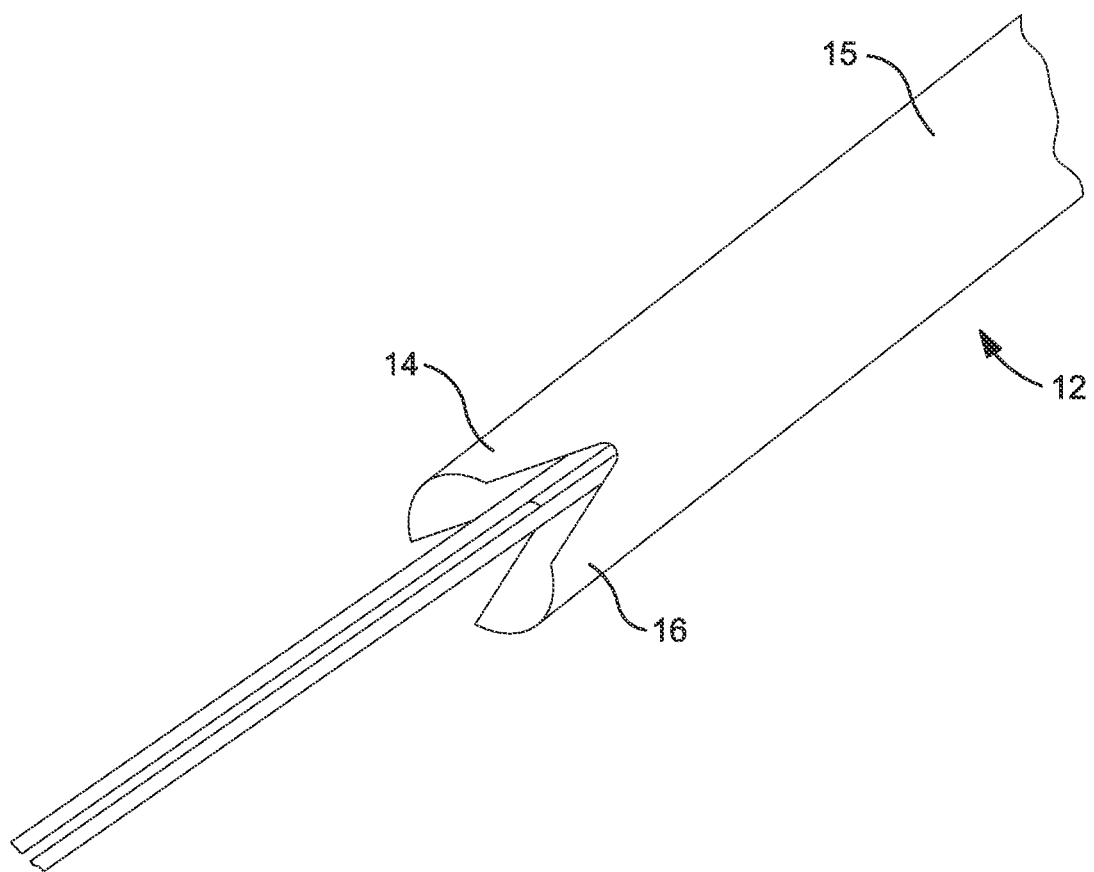
FIG. 6 is a distal, perspective view of the delivery catheter of FIG. 5.

FIGS. 5 and 6 are partial distal, perspective views of the distal portion of a delivery catheter 12 comprising a generally elongated tubular portion 15 having a generally longitudinal axis. The delivery catheter can be flexed as needed to position the distal end within a patient's bronchial airways. The distal portion of tubular portion comprises two, spaced and circumferentially opposing extensions 14, 16 comprising distal ends separated by two receiving sections comprising proximal portions 19 which do not extend distally as far as the distal ends of the extensions 14,16. The extensions are configured to extend into the adjoining target bronchial branches when the proximal portions of the relieved portions are placed into abutment or closely proximate a bronchial junction. The distal portion of delivery catheter 12 can be considered as having two notches which allow the distal extensions of the delivery catheter to extend beyond the junction of the target bronchial branches. In the embodiment shown in FIGS. 5 and 6, the outer sidewalls of the extensions 18 are aligned with the sidewalls 17 of the more proximally located tubular portion. As shown better in FIG. 6, the inside of the delivery catheter is unobstructed.

Figure 7:
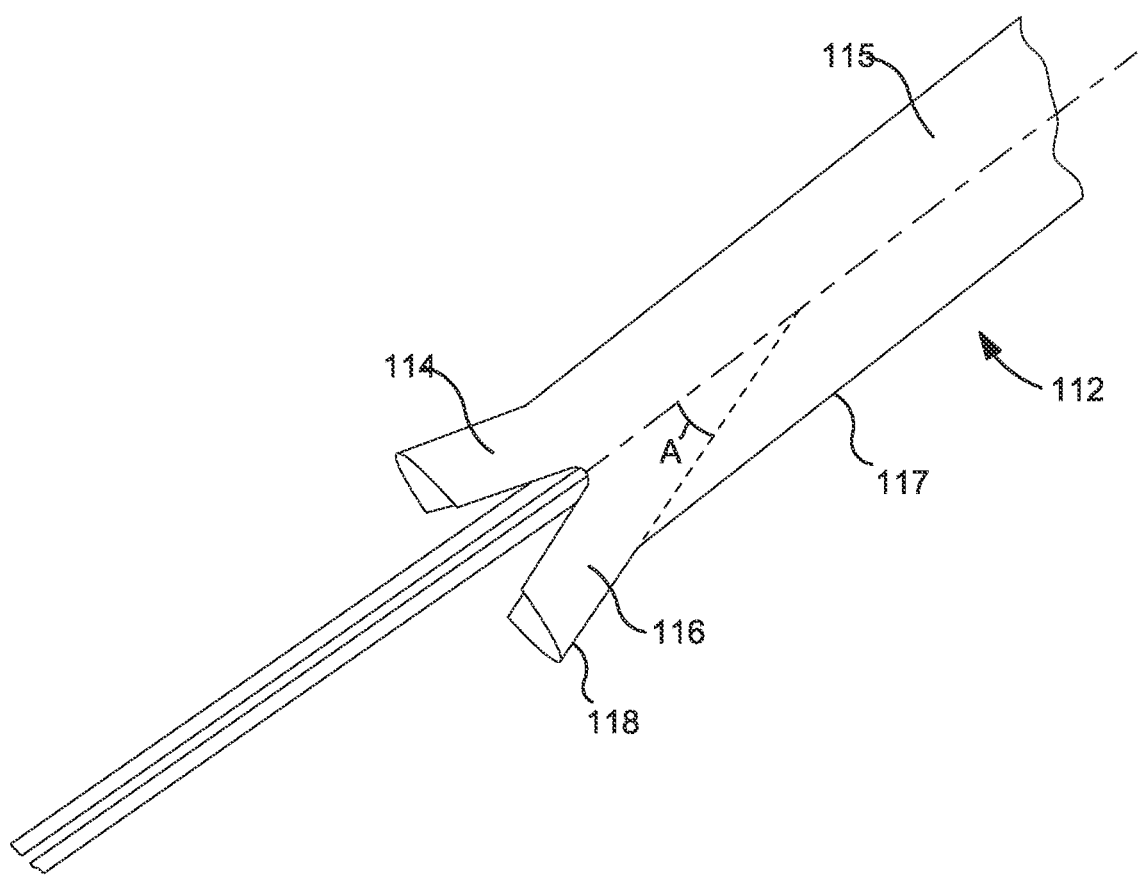
FIGS. 7 and 7A are a partial side view and a partial distal, perspective view of a delivery catheter of an alternative embodiment.
Figure 7A:
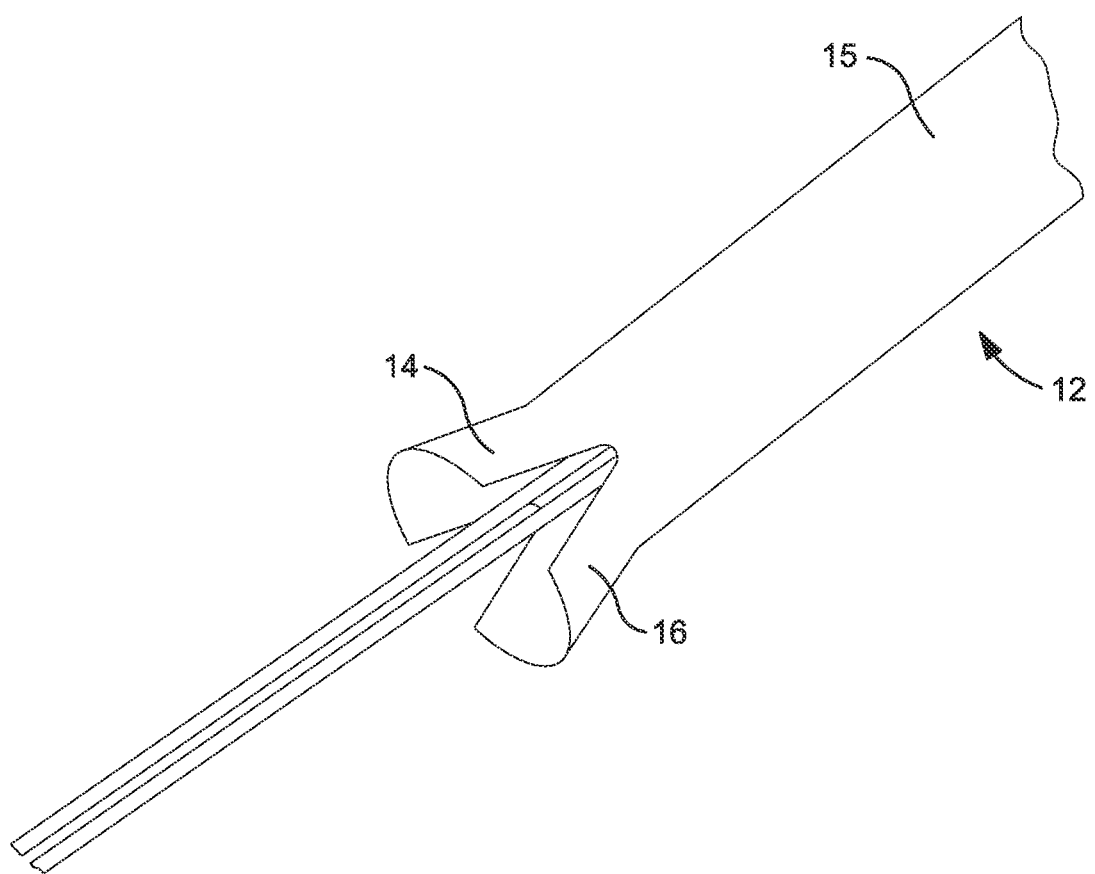

FIGS. 7 and 7A are views of an alternative delivery catheter 112 from perspectives similar to those of FIGS. 5 and 6. Delivery catheter 112 is similar to delivery catheter 12, but the extensions 114 and 116 are flared outwardly such that the outer sidewalls 118 of extensions 114, 116 are disposed at an angle to the sidewalls 117 of the more proximally located tubular portion 115. The acute angle A between an imaginary extension of the outer sidewalls of these extensions and an imaginary, central longitudinal axis passing through the tubular portion (assuming the tubular portion is in a straight configuration) is preferably about 30°-45°. As shown better in FIG. 7A, the inside of the delivery catheter is unobstructed.

Figure 8:
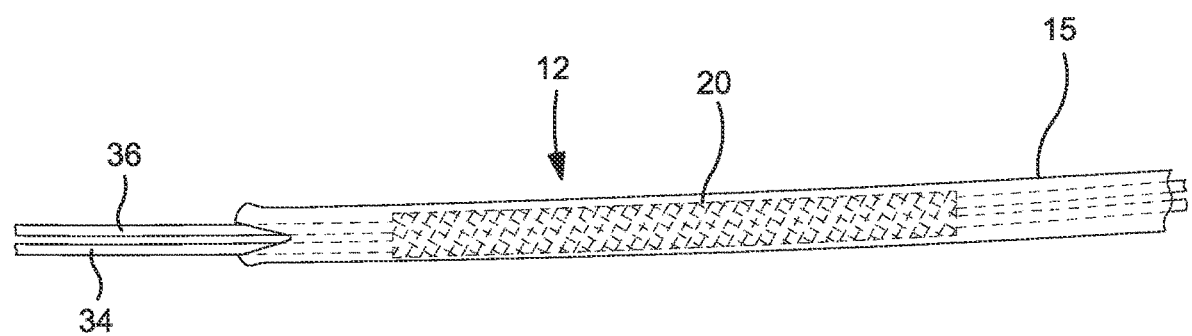
FIG. 8 is a partial front view of the catheter of FIG. 5, with portions of two guide wires and a collapsed stent shown in phantom.

FIG. 8 is a partial, distal view of the delivery catheter 12 of FIG. 5 with a collapsed Y-stent 20 (shown in phantom) positioned within the delivery catheter. Two guide wires 34 and 36 are also positioned so that they are passing through the respective branches of the Y-stent 20 and the delivery catheter 12. While the guide wires are shown extended beyond the distal end of the delivery catheter in this Figure, the distal ends of guide wires are preferably maintained within the delivery catheter until the delivery catheter has been inserted into a patient.

Figure 9:
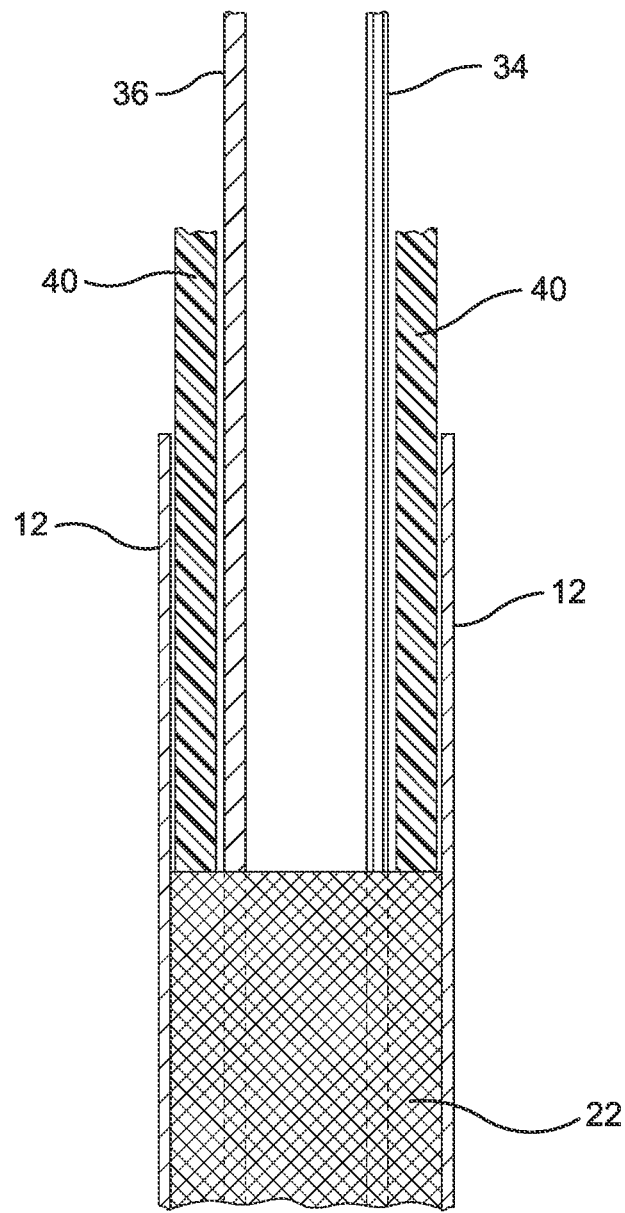
FIG. 9 is a partial, cross-sectional view of a delivery catheter, collapsed stent, plunger shaft, and two guide wires.

FIG. 9 is a partial, cross-sectional view showing the arrangement of a collapsed Y-stent 22 positioned within a delivery catheter 12 with guide wires 34 and 36 extending through the Y-stent and a plunger shaft 40 positioned proximate the proximal end of the Y-stent so that it is ready push the Y-stent out the distal end (not shown) of the delivery catheter 12. As indicated earlier, the branches of the Y-stent may have different configurations (sizes and/or shapes) in order to better fit within different bronchial tubes. Therefore, it is necessary for a surgeon to be able to discriminate between the two branches of the Y-stent. In order to facilitate the proper placement of the Y-stent, in this embodiment the guide wires are colored differently. For example, guide wire 34 is red while guide wire 36 is green. The different colors are coordinated with different branches of the Y-stent and can be observed by the surgeon via a bronchoscope prior to the placement of the delivery catheter over the anatomical junction to make sure the Y-stent is properly positioned.

Figure 10:
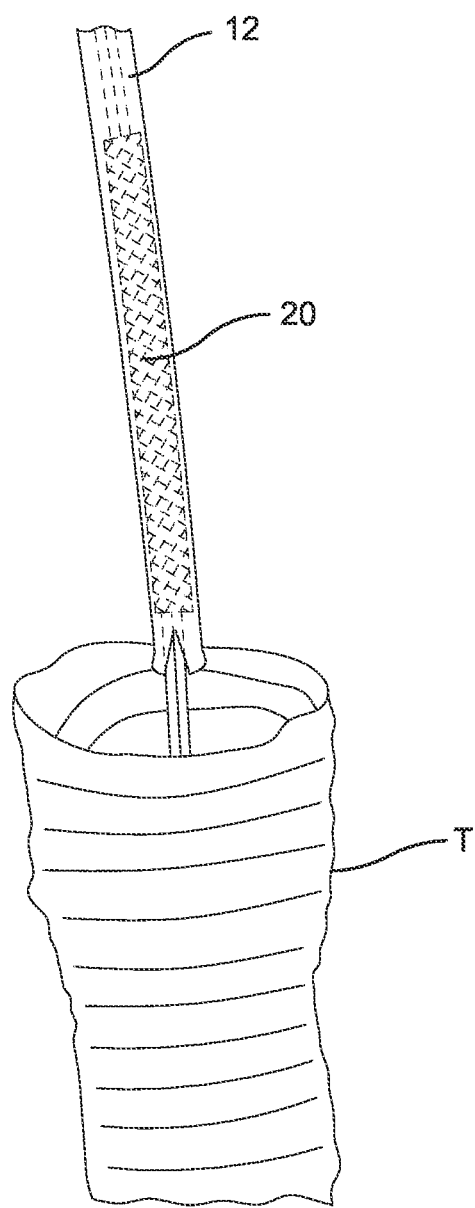
FIG. 10 is a partial, top perspective view of a delivery catheter carrying a stent (shown in phantom) through a section of a trachea.

FIG. 10 illustrates exemplary relative sizes of a delivery catheter 12 containing a collapsed Y-stent 20 and a trachea T. While delivery catheters of different diameters can by utilized, it is surgically more convenient and poses less risk to the patient if a delivery catheter having a diameter significantly smaller than the diameter of the patient's trachea is used. The use of a collapsible Y-stent allows for these advantages.

Figures 17A, 17B:
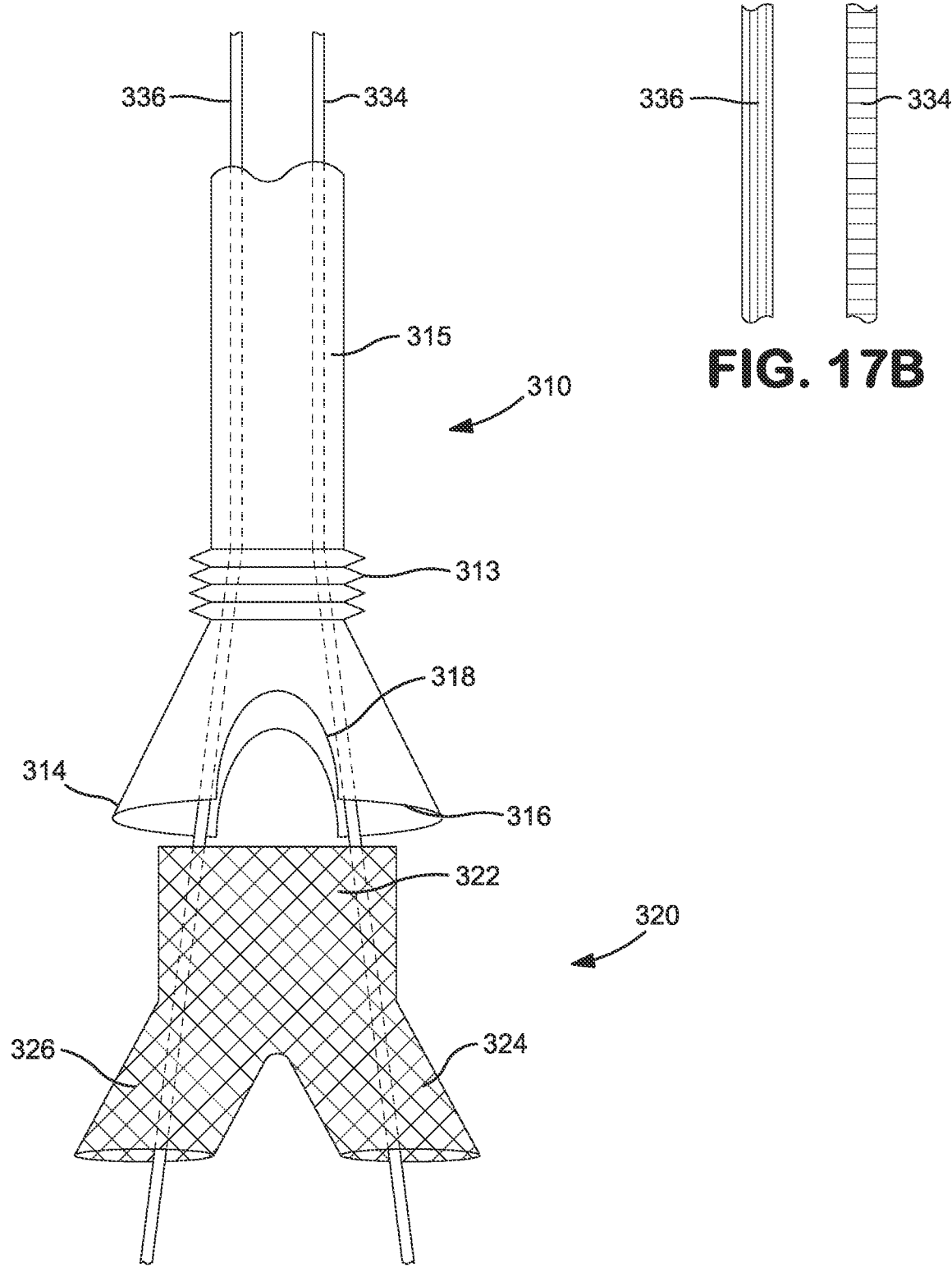
FIGS. 17A and 17B are partial, perspective and side views of a delivery catheter, Y-stent and two guide wires of a third embodiment.

FIG. 17A illustrates the distal end of another delivery catheter 310 comprising a main lumen 315, a flexible elbow portion 313 and a distal end. The flexible elbow portion 313 in this illustrated embodiment comprises corrugations in the sidewall of the catheter which facilitates the flexing of the delivery catheter around bends in the airways. As described below and illustrated in FIGS. 20 and 21, suitable steering structure may be provided. According to this illustrated embodiment, distal end is flared outwardly. This design provides more room to allow the branches of the Y-stent to begin to expand back into their fully expanded configuration prior to the trunk of the Y-stent exiting the delivery catheter 310. The distal portion of delivery catheter 310 is also provided with circumferentially-spaced extensions 314, 316 separated by receiving sections or cutouts 318. The distal end portion of delivery catheter 310 is configured to pass over the junction of the target airways. Like the other embodiments shown, the distal end of the illustrated delivery catheter is also entirely open, i.e. unobstructed, to allow the unobstructed delivery of the stent onto a bronchial junction. This open distal configuration minimizes any proximally directed forces which may be exerted on the stent by the proximal movement of the delivery catheter during placement of the Y-stent. The receiving portions allow branches of the Y-stent to be positioned in the target bronchial branches and beyond the bronchial junction prior to placement of the Y-stent and withdrawal of the delivery catheter. The catheter may have other features and structure which are not illustrated in the figures. FIG. 17B illustrates another manner of distinguishing the guide wires. In this embodiment, guide wire 336 has longitudinal stripes while guide wire 334 has circumferential stripes. These stripes can be imprinted or molded into the guide wires and are discernible by a surgeon during surgery via a bronchoscope.

FIG. 17A also illustrates Y-stent 320 comprising a trunk section 322, a right branch 324 and a left branch 326. The crosshatching indicates the woven or braided wires of the exemplary stent. Additionally, a right guide wire 334 and a left guide wire 336 extend through main lumen 315, a flexible elbow portion 313 and trunk section 322 of Y-stent 320. Right guide wire 334 extends through right branch 324 of Y-stent 320 and left guide wire 336 extends through left branch 326 of Y-stent 320. Guide wires can be formed of the same material(s) as known hydrophilic or hydrophobic guide wires.

Figure 18:
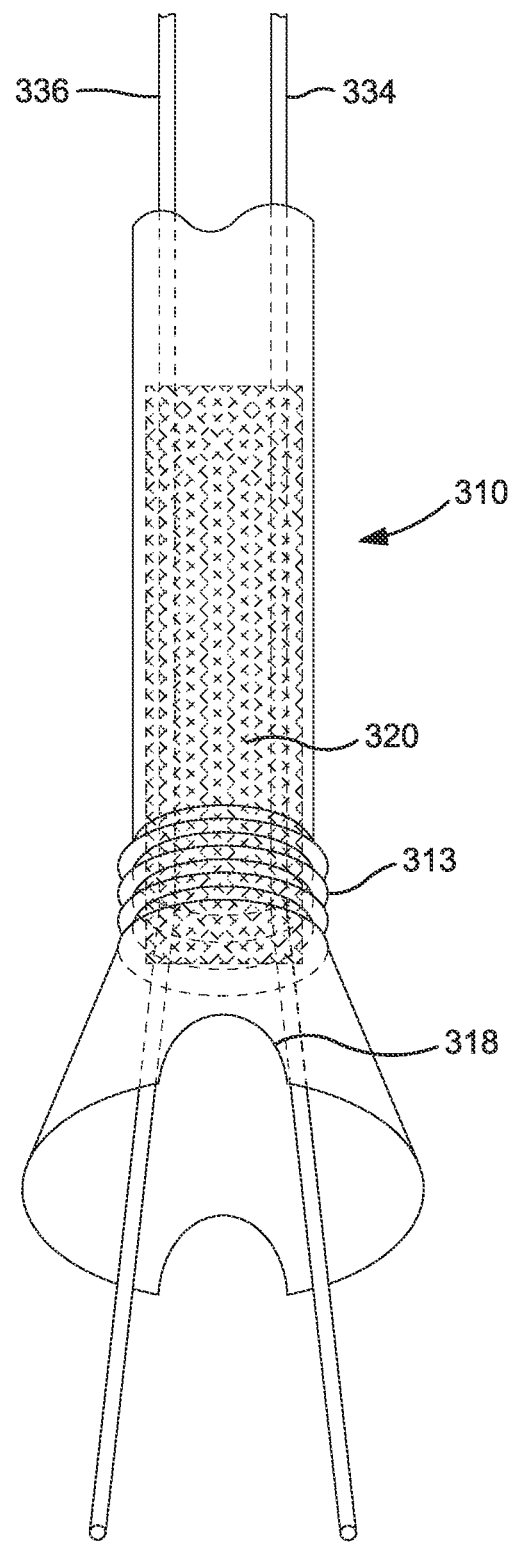
FIG. 18 is a partial bottom, perspective view of the delivery catheter, Y-stent and two guide wires of the embodiment of FIG. 15.

FIG. 18 generally illustrates the delivery catheter 310, Y-stent 320 and guide wires 334, 336 of FIG. 17A with the Y-stent 320 in a collapsed position within the delivery catheter 310.

Figure 19:
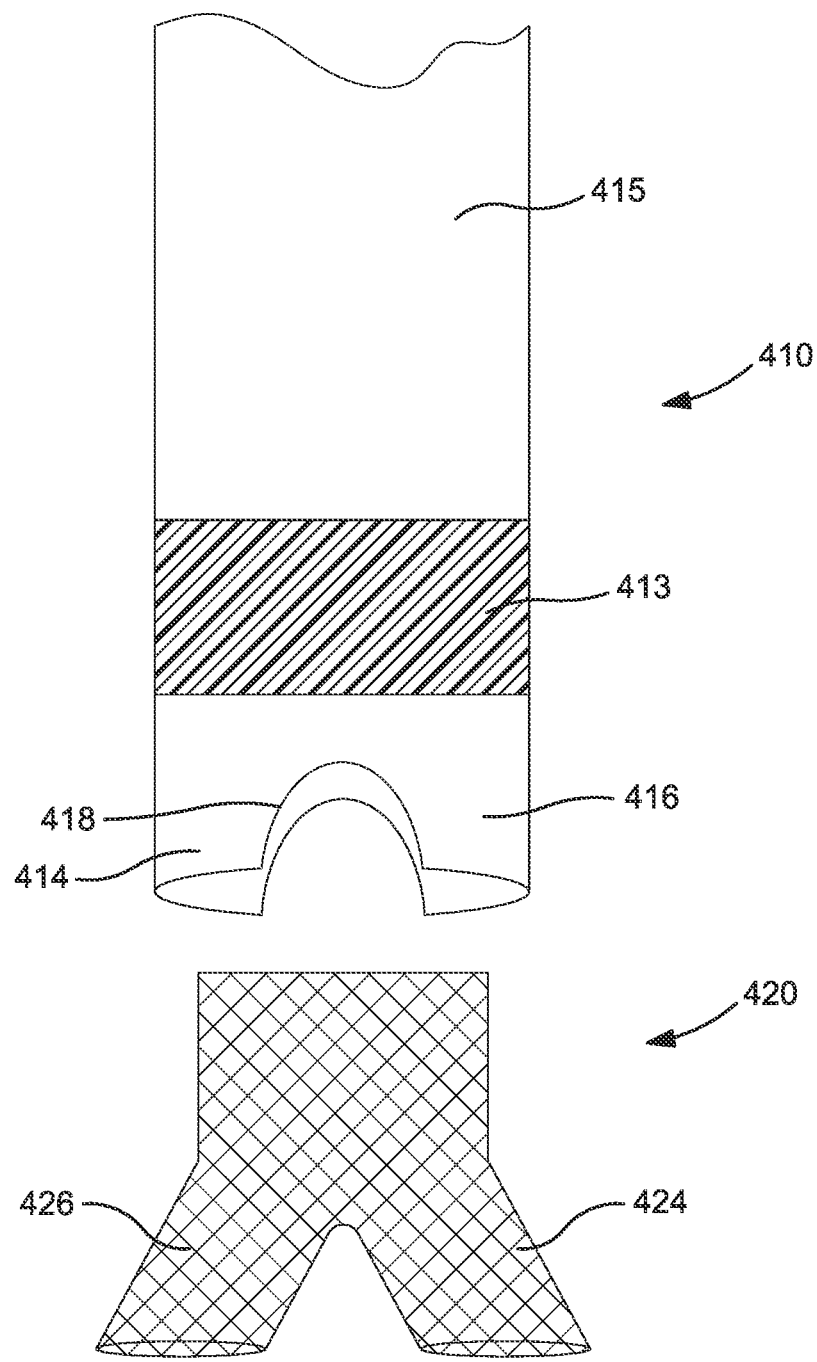
FIG. 19 is a partial, bottom perspective view of a delivery catheter and Y-stent of a fourth embodiment.

FIG. 19 illustrates an alternative delivery catheter 410 comprising a main lumen 415 a flexible portion 413 and an open distal end. The flexible portion 413 in this illustrated embodiment is formed of a resilient material, e.g. a rubber-like compound or polymer with similar flexibility and biocompatibility, which permits the catheter to flex around bends in the airways. As described above in reference to the embodiment shown in FIG. 17A, suitable steering structure may be provided. FIG. 19 also illustrates a Y-stent 420 with a wider space between the stent branches. Distal end of delivery catheter 410 has a receiving section or slot 418 configured to seat on a bronchial junction while distal extension portions 414, 416 of the delivery catheter extend beyond the bronchial junction.

Figure 20:
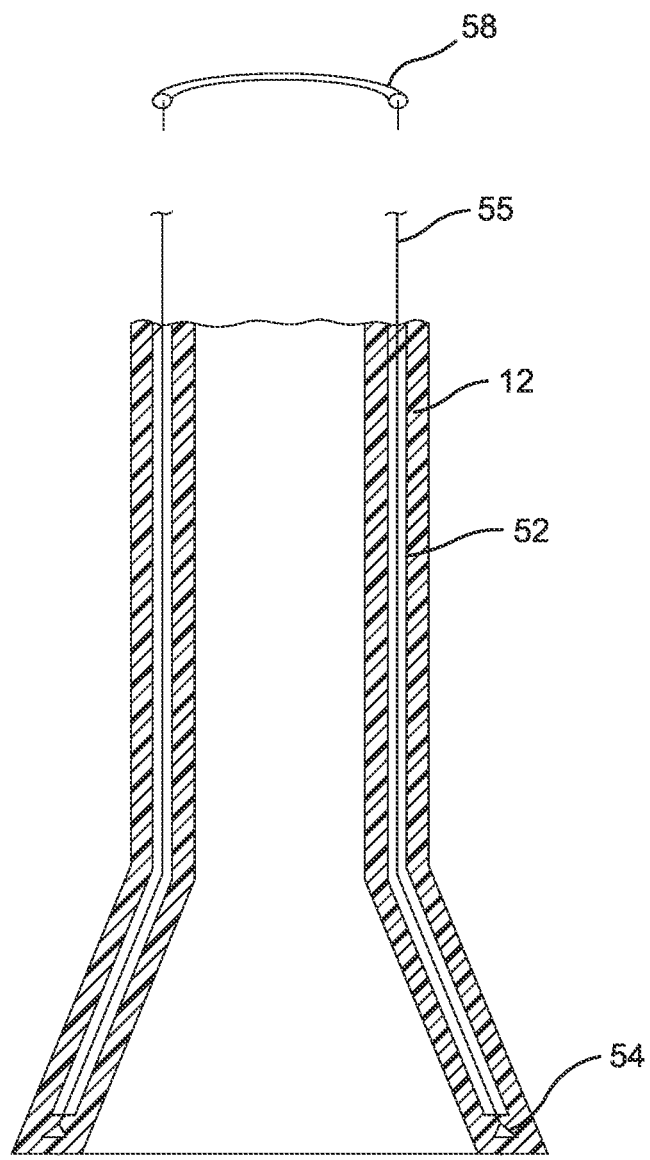
FIG. 20 is a partial, cross-sectional view of a delivery catheter with internal steering cables.
Figure 21:
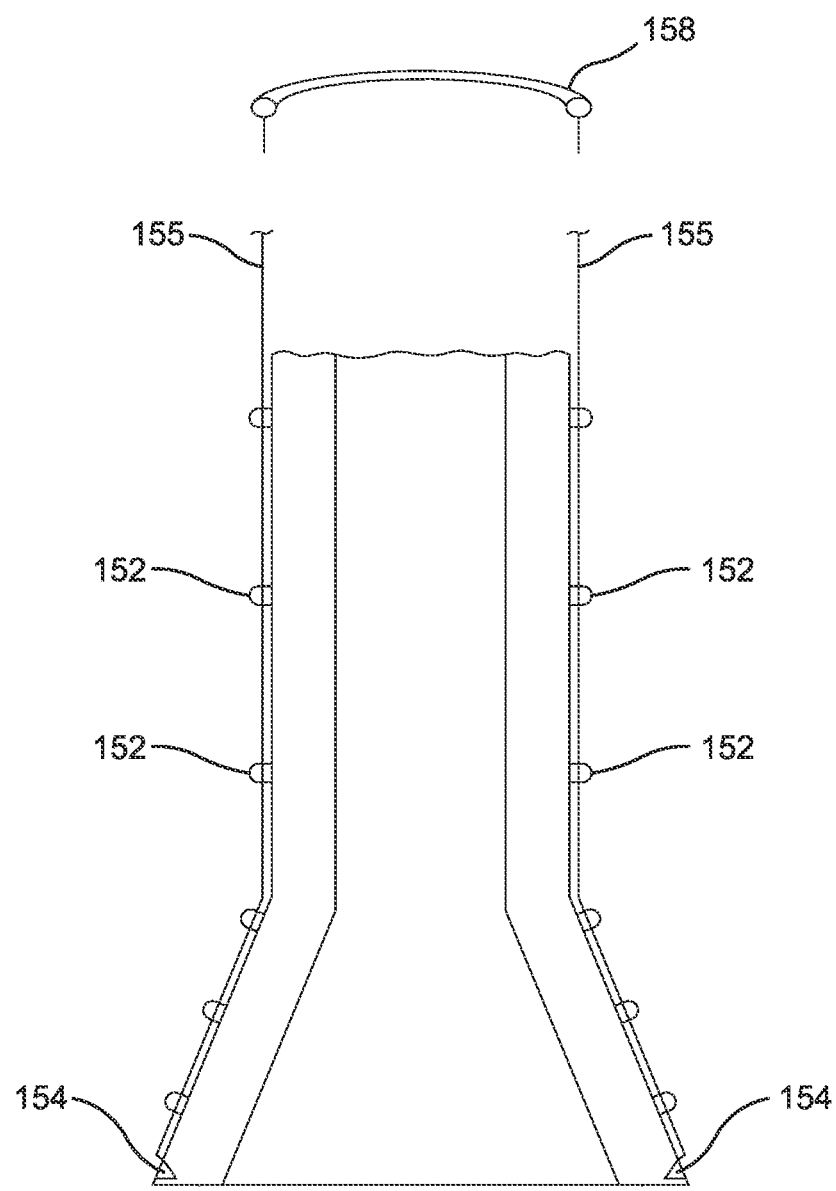
FIG. 21 is a partial, cross-sectional view of a delivery catheter with external steering cables.

FIGS. 20 and 21 indicate steering mechanisms useful with the delivery catheters. In FIG. 20, cables 55 are fixedly connected to anchors 54 embedded in the distal portions of sidewalls of the delivery catheter. Cables 55 extend through steering lumens 52 to the proximal end of the delivery catheter and terminate proximally in a steering ring 58. By manipulating the steering ring 58, a surgeon can cause the distal end of the catheter to bend in a desired direction. FIG. 21 shows a similar steering configuration, but with the cables 155 running along the external sidewall of the delivery catheter.

Figure 22:
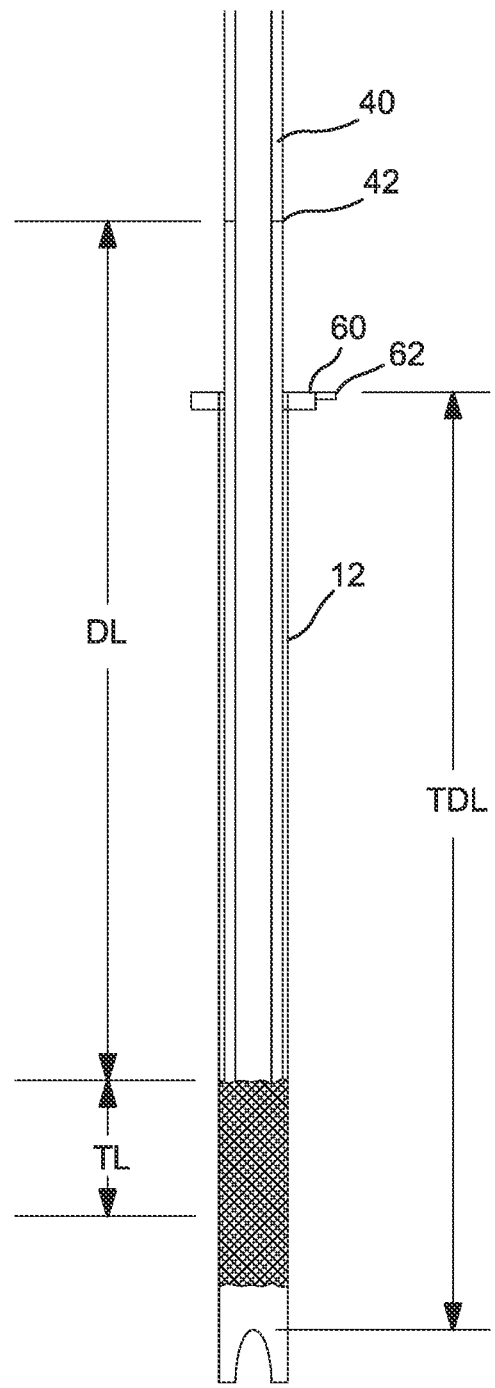
FIG. 22 is a partial cross-sectional view of a delivery catheter, collapsed stent, plunger shaft and guide wires of an another embodiment.
Figure 23A:
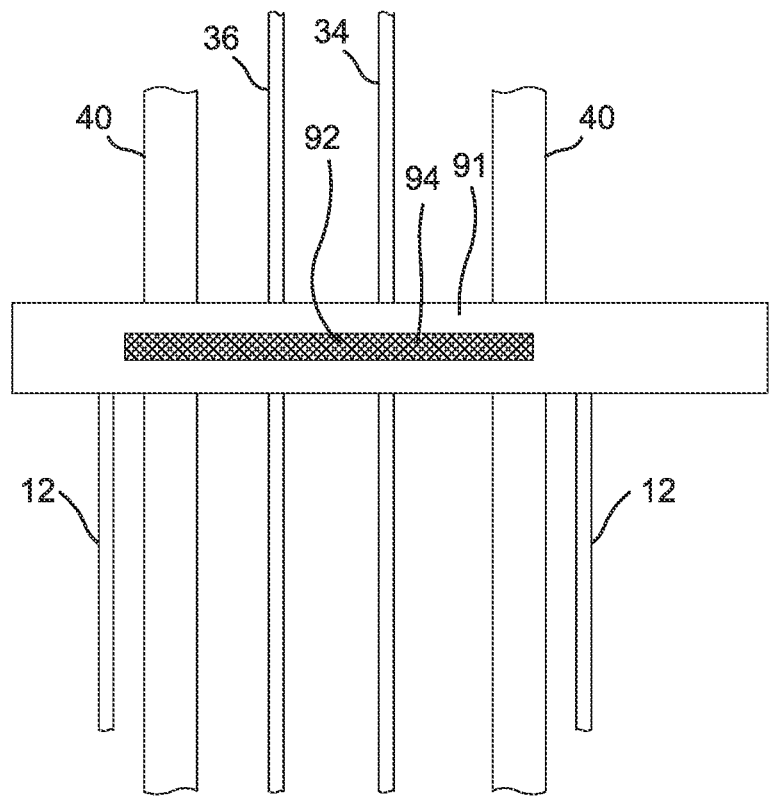
FIGS. 23A and 23B are partial side and top views, respectively, of the proximal end of a delivery catheter illustrating a fixation device for releasably securing the plunger shaft and guide wires.
Figure 23B:
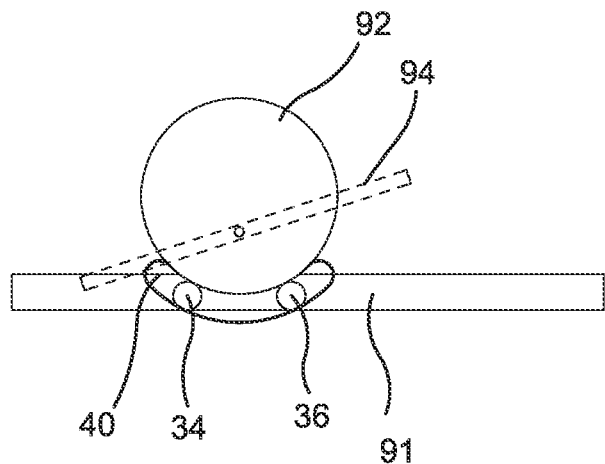

FIGS. 22, 23A and 23B illustrate other optional features of the components. FIG. 22 shows a handle structure 60 having a position indicator knob 62 for indicating the orientation of the delivery catheter, i.e. distinguishing between the different sides of the delivery catheter, to the surgeon. Handle structure 60 is also at a location TDL or tubular delivery length (TDL) which is equal to the distance from the proximal portion of one of said receiving sections to this indicated location. While this embodiment indicates the location TDL with structure, i.e. the handle structure, the location TDL can also be "marked" or indicated with some other visible indicia such as a line or other marking. FIG. 22 also indicates position DL on the plunger shaft 40. DL is the delivery length, i.e. the distance the plunger shaft should be inserted into the catheter to fully seat the Y-stent on the anatomical junction. Distance DL is equal to distance TDL minus distance TL and gives the surgeon a convenient reference for seeing how the plunger shaft should be advanced relative to the delivery catheter.

FIGS. 23A and 23B illustrate a fixation device 90 in the form of a cam wheel which is used to releasably secure the positions of the plunger shaft and/or guide wires relative to the delivery catheter prior to the desired deployment of the guide wires and stent during surgery. Fixation device 90 comprises a frame 91 with an inclined slot 94 which guides a locking wheel 92 between an advanced position which engages and squeezes plunger shaft 40 and guide wires 34,36, and a withdrawn position which does not interfere with the relative movement of the plunger and guide wires relative to the delivery catheter. Frame 91 is connected to delivery catheter 12. Fixation device 90 reduces the risk of the stent being prematurely deployed or the guide wires slipping out of the delivery catheter prior to surgery.

Methods comprise the step of providing a collapsible, preferably porous Y-stent, preferably formed of nitinol wire, collapsing the Y-stent, disposing the Y-stent in a delivery catheter, positioning the delivery catheter in an airway proximate a junction and displacing the Y-stent from the delivery catheter at least partially into two airways. Another step comprises positioning the distal end of the delivery catheter over the junction of the airway, e.g. over a portion of the carina, with the receiving portions seated on the anatomical junction and the outer portions of the distal end and the branches of the stent positioned distally of the bronchial junction. Another step comprises positioning two guide wires down the same lumen of the delivery catheter, into the trunk of the Y-stent and one each of the guide wires into the legs of the Y-stent. One method comprises the step of extending the guide wires distally into the target airways prior to the displacement of the Y-stent from the delivery catheter in order to guide the branches of the Y-stent into the proper airway. One method comprises the step of positioning a Y-stent at least partially into two airways. One method comprises the step of positioning a Y-stent at the junction of two airways. One method comprises advancing the plunger shaft within the delivery catheter to advance the stent into the distal end of the delivery catheter. A preferred method comprises the step of positioning a Y-stent over the junction separating two airways so that one branch of the Y-stent extends at least partially into one airway and the other branch of the Y-stent extends at least partially into the other airway. As the delivery catheter is withdrawn proximally, the branches of the Y-stent are free to expand before the trunk of the stent expands.

Figure 11:
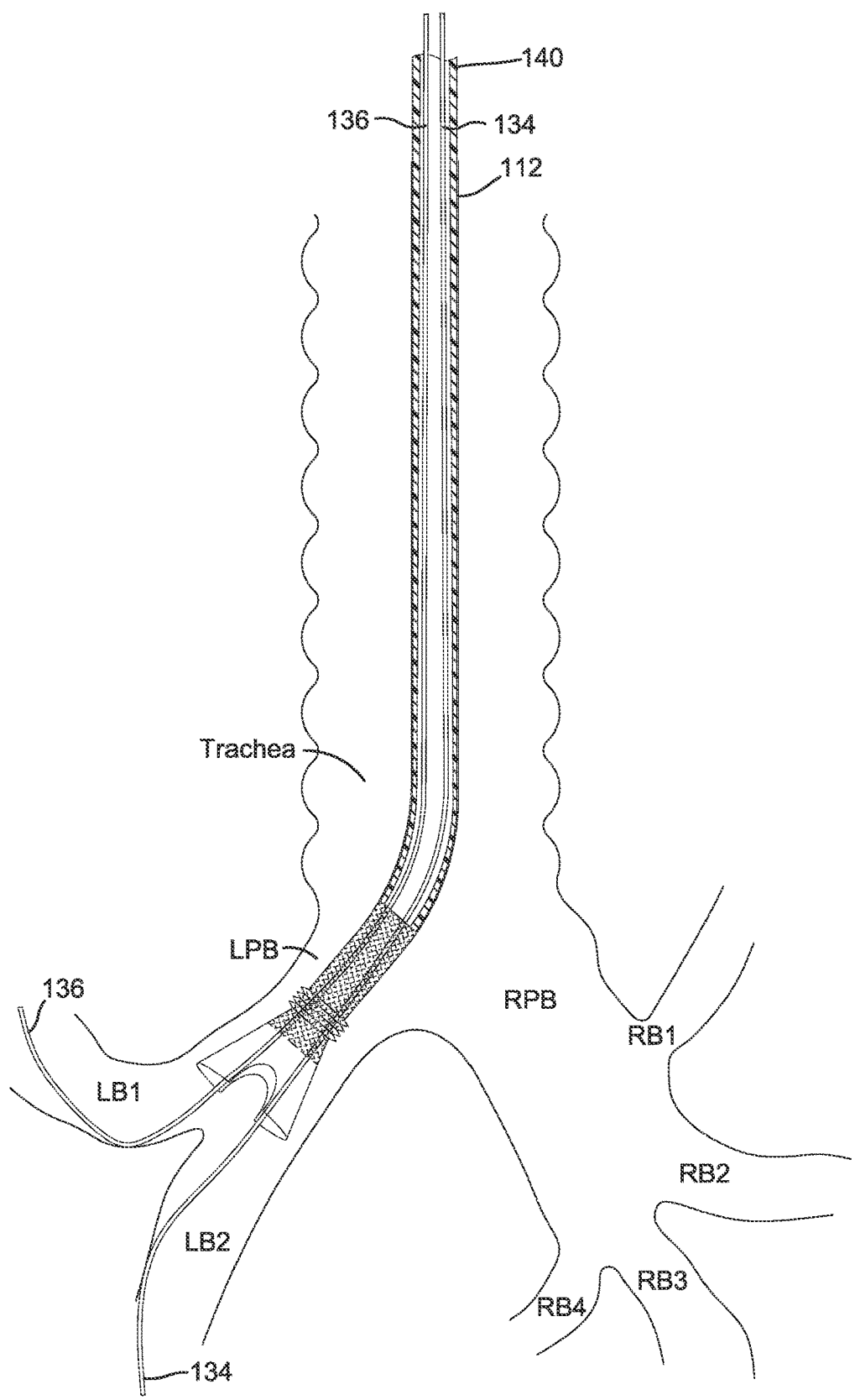
FIG. 11 is an illustration of a delivery catheter with two guide wires and a collapsed Y-stent positioned within a patient's lungs prior to final positioning of the catheter.

FIGS. 11-16 illustrate the delivery catheter, stent, plunger shaft and guide wires of FIG. 17A at different times during a surgical procedure. FIG. 11 shows the delivery catheter positioned proximate an airway junction prior to placement of a Y-stent. The Y-stent is shown in phantom. The guide wires 134, 136 have been extended out of the distal end of the delivery catheter into two target branch airways.

Figure 12:
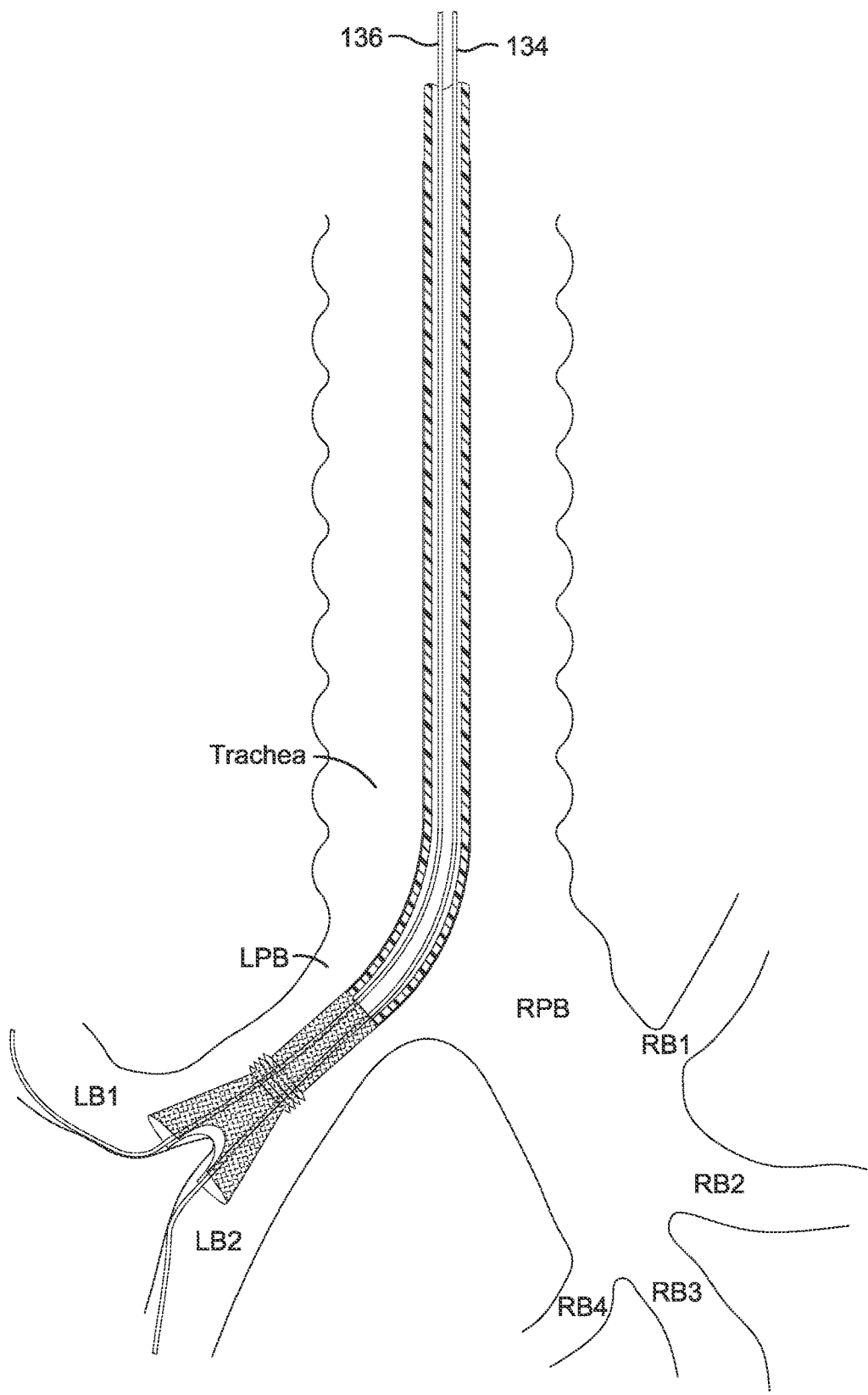
FIG. 12 is an illustration of a delivery catheter, guide wires and Y-stent of FIG. 10 within a patient's lung positioned for placement of a Y-stent.

FIG. 12 illustrates the delivery catheter in a more distal position with the receiving portions on the bronchial junction and the extensions of the catheter positioned in the respective branch airways. The stent has been advanced in the delivery catheter and has started to expand to conform to the inner walls of the distal end of the delivery catheter.

Figure 13:
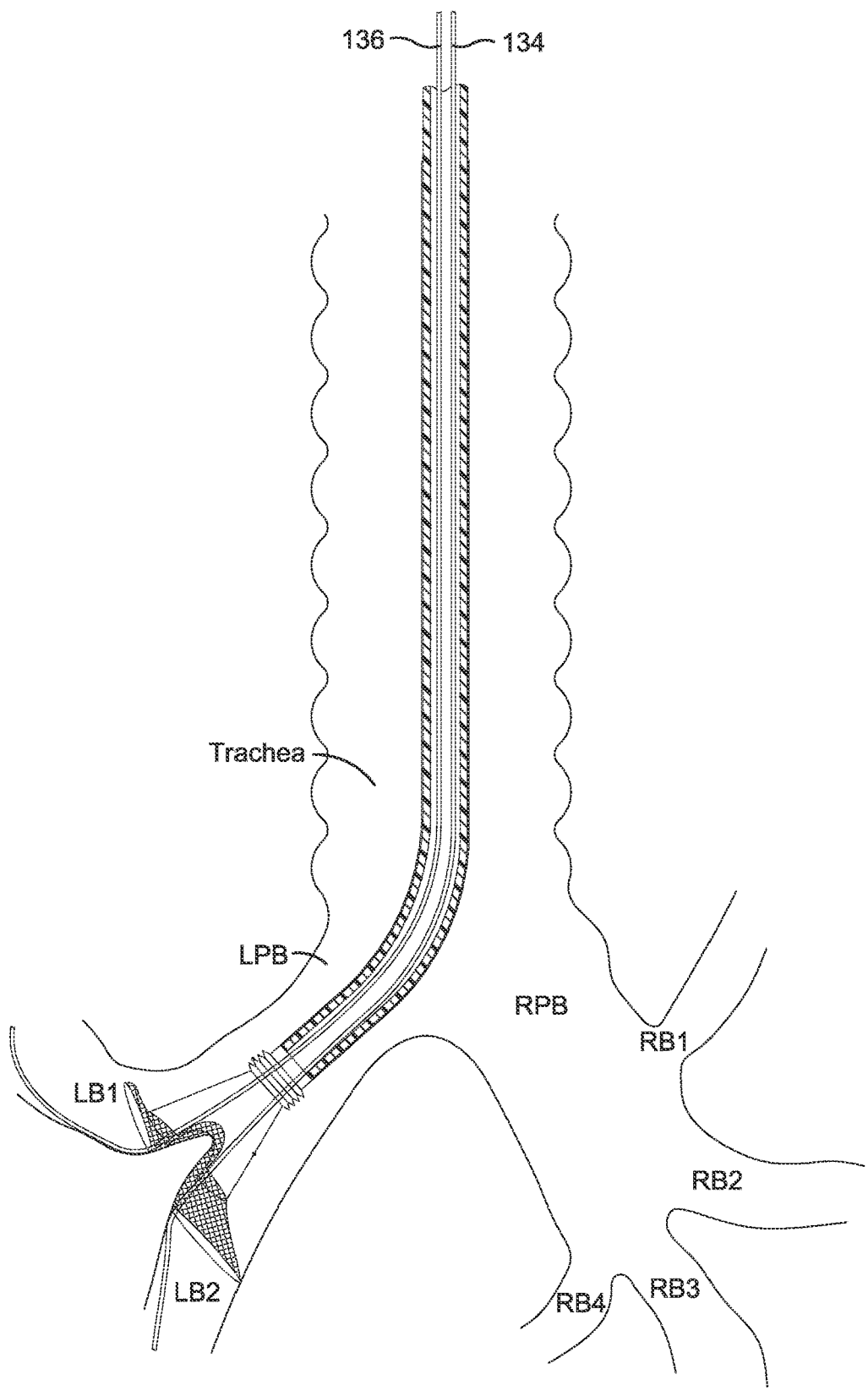
FIG. 13 is an illustration of the delivery catheter, stent and guide wires of FIG. 10 within a patient's lungs after the stent has started to emerge from the distal end of the delivery catheter.

FIG. 13 shows the stent partially beyond the distal end of the delivery catheter. As indicated, the stent expands toward its normal, uncompressed configuration when the restrictive forces of the delivery catheter are removed.

Figure 14:
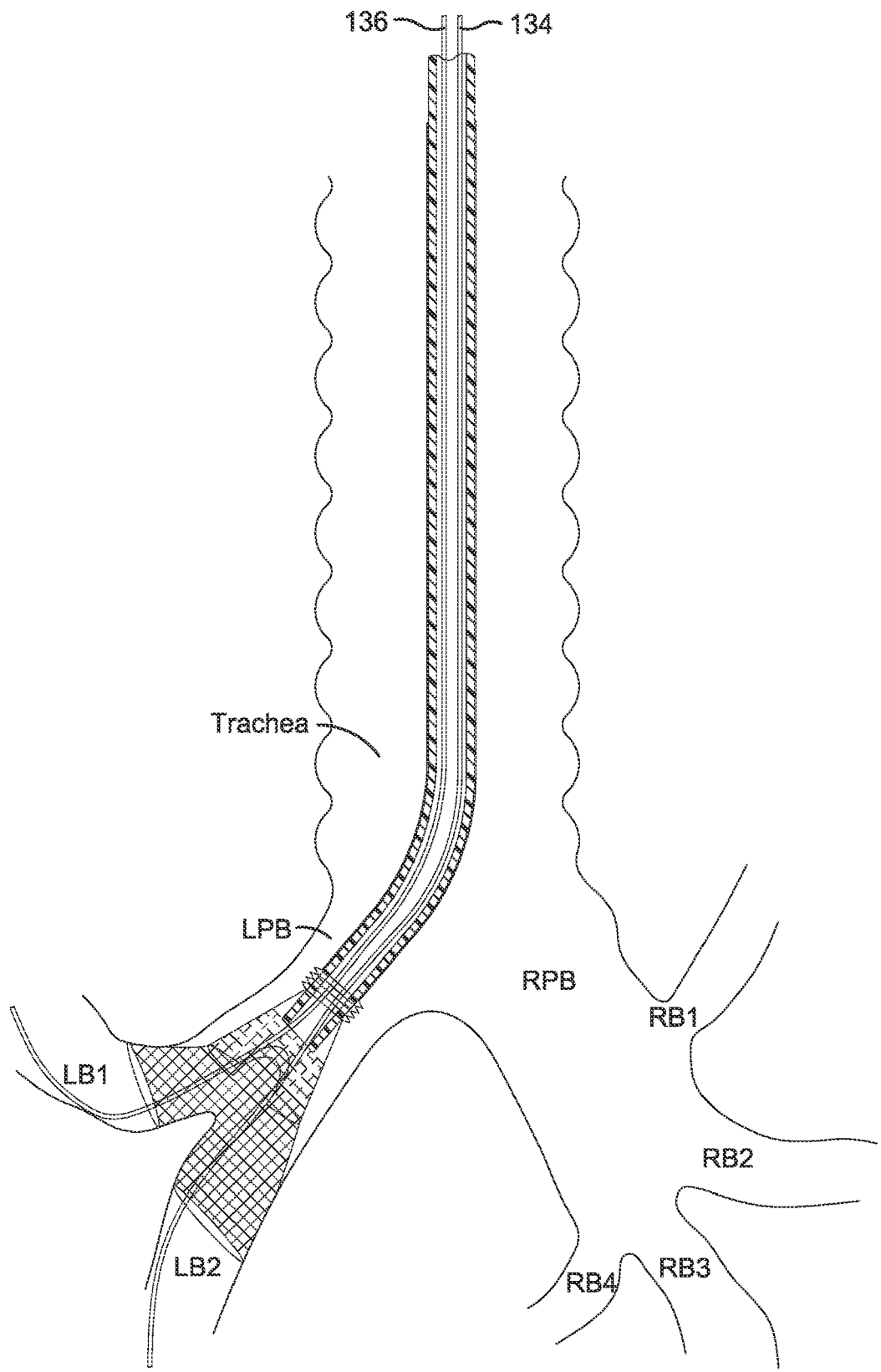
FIG. 14 illustrates the delivery catheter, stent and guide wires of FIG. 10 within a patient's lungs with the Y-stent deployed further distally than in FIG. 13 and with the catheter partially withdrawn.

FIG. 14 shows the delivery catheter partially withdrawn while the stent is maintained in place by the plunger shaft and the frictional forces between the partially expanded Y-stent and the bronchial walls. As noted above, the unobstructed internal distal end of the delivery catheter does not apply any unwanted proximally-directed forces on the stent during this deployment.

Figure 15:
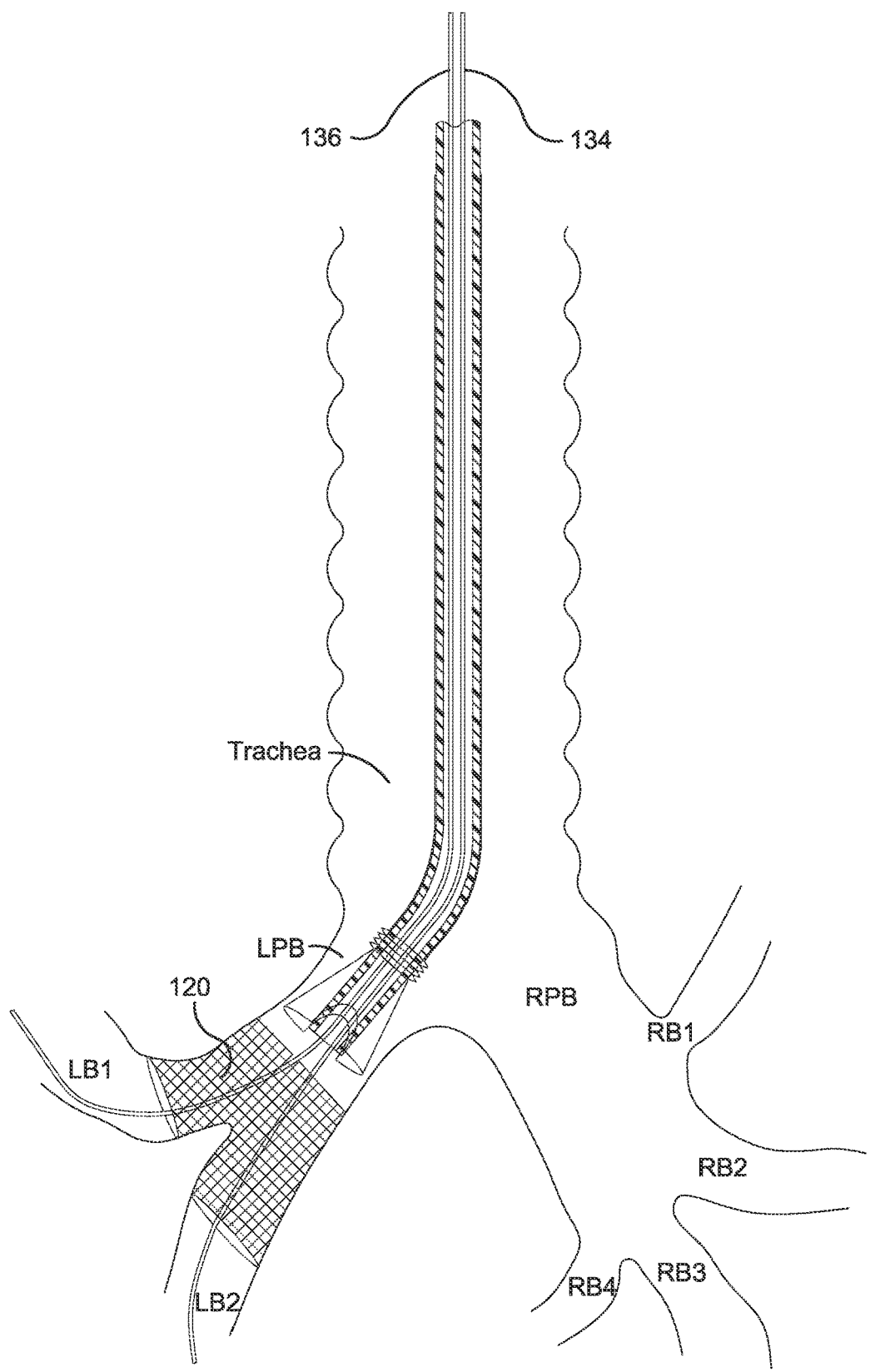
FIG. 15 is an illustration of the delivery catheter, plunger shaft and guide wires of FIG. 10 being withdrawn after placement of the Y-stent.

FIG. 15 illustrates the delivery catheter withdrawn from the Y-stent and the Y-stent properly positioned over the junction of the target airways.

Specifically, Y-stent 120 is positioned with one branch of the Y-stent in each of the target airways and the trunk section in the feeding airway.

Figure 16:
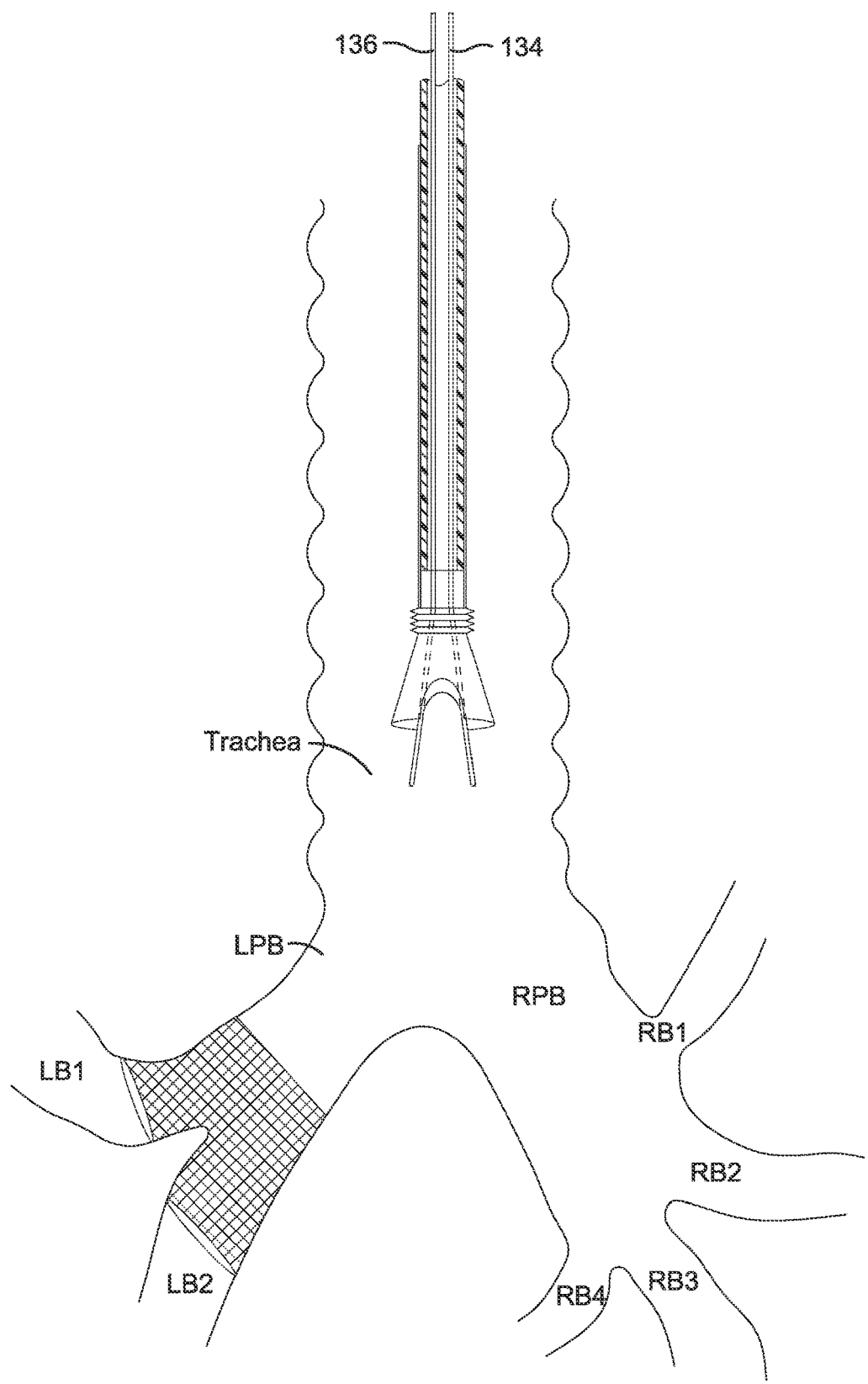
FIG. 16 is an illustration of the delivery catheter, plunger shaft and guide wires of FIG. 10 further withdrawn after placement of the Y-stent.

FIG. 16 shows the delivery catheter further withdrawn and the guide wires fully withdrawn from the properly placed Y-stent.

Different size delivery catheters with different sized and shaped relieved portions can be used for different patients. Also, according to one version of the delivery catheter, the distal ends of extensions extensions extend at least 1 cm beyond the proximal portions of the receiving sections. According to another version of the delivery catheter, the distal ends of the extensions extend at least 1.5 cm beyond the proximal portions of the receiving sections. The disclosed stents, delivery apparatus and methods are intended for use in humans and other mammals, such as dogs.

The open configuration of the distal end of the disclosed delivery catheters minimizes any proximally directed forces on the properly positioned stent by the withdrawing catheter. Additionally, since the branches of the stent can expand while the trunk of the stent is still positioned in the catheter as the stent is being forced out of the delivery catheter, the stent will be less likely to spring proximally and become dislodged from the desired position where the crotch of the stent abuts the bronchial junction.

The invention claimed is:

1. A delivery catheter for a Y-stent configured to maintain patency between an anatomical trunk conduit and two anatomical branch conduits separated by a junction, said delivery catheter comprising:
   a tubular portion comprising, a proximal portion and a distal portion;
   said distal portion comprising two, spaced and circumferentially opposing extensions defining a single, permanently unobstructed, distal opening;
   said extensions comprising distal ends;
   said tubular portion and said extensions comprising inner walls;
   said extensions are separated by two receiving sections configured to receive an anatomical conduit junction when said extensions extend into adjacent anatomical branch conduits, said receiving sections comprising proximal portions which do not extend distally as far as the distal ends of said extensions, and wherein said extensions are configured to extend into adjoining anatomical branch conduits when said proximal portions of said receiving sections are abutting a junction; and
   said distal opening of the delivery catheter, including said receiving portions, is completely and permanently unobstructed by any structure of the delivery catheter so that the only forces which need to be overcome when deploying a stent from the delivery catheter are the frictional forces between the Y-stent and the inner walls of the delivery catheter.

2. A delivery catheter according to claim 1 wherein said distal ends of said extensions extend at least 1 cm beyond said proximal portions of said receiving sections.

3. A delivery catheter according to claim 1 wherein said distal ends of said extensions extend at least 1.5 cm beyond said proximal portions of said receiving sections.

4. A delivery catheter according to claim 1 wherein said tubular portion comprises outer sidewalls, said extensions comprise outer sidewalls and said outer sidewalls of said extensions are contiguous and permanently aligned with said outer sidewalls of said tubular portion.

5. A delivery catheter according to claim 1 wherein said tubular portion comprises a substantially longitudinal axis and outer sidewalls, said extensions comprise outer sidewalls and said outer sidewalls of said extensions are angled outwardly relative to said outer sidewalls of said tubular portion.

6. A delivery catheter according to claim 5 wherein said outer sidewalls of said extensions form an acute angle of about 30° to about 45° with said longitudinal axis.

7. A delivery catheter according to claim 5 wherein said outer sidewalls of said extensions are contiguous with said outer sidewalls of said tubular portion.

* * * * *